United States Patent
Quirk et al.

(10) Patent No.: US 7,041,787 B2
(45) Date of Patent: May 9, 2006

(54) DESIGN AND USE OF ADVANCED ZINC CHELATING PEPTIDES TO REGULATE MATRIX METALLOPROTEINASES

(75) Inventors: Stephen Quirk, Alpharetta, GA (US); David John Tyrrell, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 988 days.

(21) Appl. No.: 09/753,139

(22) Filed: Dec. 29, 2000

(65) Prior Publication Data

US 2003/0073808 A1   Apr. 17, 2003

(51) Int. Cl.
- A61K 38/00   (2006.01)
- A61K 38/04   (2006.01)
- C12N 15/09   (2006.01)

(52) U.S. Cl. .................. 530/323; 530/330; 514/17; 435/69.2; 930/250

(58) Field of Classification Search .............. 435/69.2, 435/219, 226; 530/300, 330, 323; 514/12, 514/16, 17; 930/250
See application file for complete search history.

(56) References Cited

U.S. PATENT DOCUMENTS

| | | |
|---|---|---|
| 4,868,108 A | 9/1989 | Bahar et al. |
| 4,883,760 A | 11/1989 | Heelies |
| 4,943,522 A | 7/1990 | Eisinger et al. |
| 4,956,302 A | 9/1990 | Gordon et al. |
| 4,999,285 A | 3/1991 | Stiso |
| 5,037,735 A | 8/1991 | Khanna et al. |
| 5,141,850 A | 8/1992 | Cole et al. |
| 5,188,938 A | 2/1993 | Khanna et al. |
| 5,270,168 A | 12/1993 | Grinnell |
| 5,275,785 A | 1/1994 | May et al. |
| 5,324,634 A | 6/1994 | Zucker |
| 5,332,479 A | 7/1994 | Uenoyama et al. |
| 5,354,447 A | 10/1994 | Uenoyama et al. |
| 5,354,692 A | 10/1994 | Yang et al. |
| 5,382,346 A | 1/1995 | Uenoyama et al. |
| 5,415,994 A | 5/1995 | Imrich et al. |
| 5,464,822 A | 11/1995 | Christophers et al. |
| 5,496,453 A | 3/1996 | Uenoyama et al. |
| 5,541,069 A | 7/1996 | Mortensen et al. |
| 5,559,041 A | 9/1996 | Kang et al. |
| 5,569,608 A | 10/1996 | Sommer |
| 5,602,040 A | 2/1997 | May et al. |
| 5,622,871 A | 4/1997 | May et al. |
| 5,641,636 A | 6/1997 | Strauss, III et al. |
| 5,656,503 A | 8/1997 | May et al. |
| 5,670,381 A | 9/1997 | Jou et al. |
| 5,698,404 A | 12/1997 | Strauss, III et al. |
| 5,698,671 A | 12/1997 | Stetler-Stevenson et al. |
| 5,710,005 A | 1/1998 | Rittenburg |
| 5,712,172 A | 1/1998 | Huang et al. |
| 5,731,162 A | 3/1998 | Gatti et al. |
| 5,734,014 A | 3/1998 | Ishima et al. |
| 5,736,341 A | 4/1998 | Sorsa et al. |
| 5,741,659 A | 4/1998 | Ralls et al. |
| 5,766,961 A | 6/1998 | Pawlak et al. |
| 5,770,460 A | 6/1998 | Pawlak et al. |
| 5,770,691 A | 6/1998 | Fields et al. |
| 5,798,273 A | 8/1998 | Shuler et al. |
| 5,869,277 A | 2/1999 | Stetler-Stevenson et al. |
| 5,876,944 A | 3/1999 | Kuo |
| 5,879,951 A | 3/1999 | Sy |
| 5,895,765 A | 4/1999 | Rheinheimer et al. |
| 5,916,521 A | 6/1999 | Bunce et al. |
| 5,922,550 A | 7/1999 | Everhart et al. |
| 5,939,331 A | 8/1999 | Burd et al. |
| 5,985,675 A | 11/1999 | Charm et al. |
| 5,989,921 A | 11/1999 | Charlton et al. |
| 6,060,256 A | 5/2000 | Everhart et al. |
| 6,074,869 A | 6/2000 | Pall et al. |
| 6,127,139 A | 10/2000 | Te Koppele et al. |
| 6,136,610 A | 10/2000 | Polito et al. |
| 6,140,134 A | 10/2000 | Rittenburg |
| 6,143,506 A | 11/2000 | Golub et al. |
| 6,156,271 A | 12/2000 | May |
| 6,180,288 B1 | 1/2001 | Everhart et al. |
| 6,183,972 B1 | 2/2001 | Kuo et al. |
| 6,194,221 B1 | 2/2001 | Rehg et al. |
| 6,203,757 B1 | 3/2001 | Lu et al. |

(Continued)

FOREIGN PATENT DOCUMENTS

DE   4000-797 A   1/1990

(Continued)

OTHER PUBLICATIONS

Hurst et al. "Development and Characterization of a New Polyclonal Antibody Specifically Against Tissue Inhibitor of Metalloproteinases 4 in Human Breast Cancer" Biochem Biophys Res Commun, Feb. 16, 2001, 166-171 281(1), PMID 11178975.

(Continued)

*Primary Examiner*—Rebecca E. Prouty
*Assistant Examiner*—Malgorzata A. Walicka
(74) *Attorney, Agent, or Firm*—Schwegman, Lundberg, Woessner & Kluth, P.A.

(57) ABSTRACT

The present invention relates to MMP regulators that comprise new synthetic peptides, that comprise amino acid sequences structurally similar to those of MMP binding region of TIMPs, coupled to zinc chelators. The invention also relates to methods for making these MMP regulators and their use for the treatment of chronic and acute wounds and for the treatment of angiogenesis-associated diseases.

5 Claims, 8 Drawing Sheets

U.S. PATENT DOCUMENTS

| | | |
|---|---|---|
| 6,221,579 B1 | 4/2001 | Everhart et al. |
| 6,225,127 B1 | 5/2001 | Thompson et al. |
| 6,235,539 B1 | 5/2001 | Carpenter |
| 6,258,548 B1 | 7/2001 | Buck |
| 6,274,703 B1 | 8/2001 | Goldberg |
| 6,280,687 B1 | 8/2001 | Golub et al. |
| 6,294,344 B1 | 9/2001 | O'Brien |
| 6,297,020 B1 | 10/2001 | Brock |

FOREIGN PATENT DOCUMENTS

| | | |
|---|---|---|
| EP | 0 306 772 A1 | 3/1989 |
| EP | 0 398 621 A2 | 11/1990 |
| EP | 0 462 182 B1 | 12/1991 |
| EP | 0 296 724 B1 | 1/1995 |
| EP | 0 833 159 A2 | 4/1998 |
| EP | 0 884 393 A1 | 12/1998 |
| GB | 2 147 206 A | 5/1995 |
| JP | 63210665 A | 9/1988 |
| JP | 04-183397 A2 | 6/1992 |
| JP | 06167497 A | 8/1992 |
| JP | 05034353 A | 2/1993 |
| JP | 05-244985 A2 | 9/1993 |
| JP | 06213888 A | 8/1994 |
| JP | 06300757 A | 10/1994 |
| JP | 08136548 A | 11/1994 |
| JP | 08226918 A | 2/1995 |
| JP | 07159402 A | 6/1995 |
| JP | 09136841 A | 8/1995 |
| JP | 09206099 A | 1/1996 |
| JP | 08201392 A | 8/1996 |
| JP | 08217800 A | 8/1996 |
| JP | 10160736 A | 9/1996 |
| JP | 10232189 A | 2/1997 |
| JP | 09087299 A | 3/1997 |
| JP | 409249700 A | 9/1997 |
| JP | 10287700 A | 10/1998 |
| JP | 10313896 A | 12/1998 |
| JP | 11083858 A | 3/1999 |
| JP | 11318449 A | 3/1999 |
| WO | WO90/10062 | 2/1989 |
| WO | WO91/11714 | 1/1990 |
| WO | WO90/10228 | 9/1990 |
| WO | WO90/11287 | 10/1990 |
| WO | WO92/12428 | 1/1991 |
| WO | WO99/12333 | 8/1991 |
| WO | WO92/11021 | 7/1992 |
| WO | WO94/01775 | 7/1992 |
| WO | WO92/13096 | 8/1992 |
| WO | WO/13874 | 8/1992 |
| WO | WO94/10208 | 10/1992 |
| WO | WO95/30903 | 5/1994 |
| WO | WO96/33413 | 4/1995 |
| WO | WO97/06439 | 8/1995 |
| WO | WO98/22800 | 11/1996 |
| WO | WO98/23958 | 11/1996 |
| WO | WO97/00449 | 1/1997 |
| WO | WO97/04080 | 2/1997 |
| WO | WO98/39657 | 6/1997 |
| WO | WO97/25437 | 7/1997 |
| WO | WO98/04287 | 2/1998 |
| WO | WO98/46787 | 4/1998 |
| WO | WO98/29560 | 7/1998 |
| WO | WO98/40475 | 9/1998 |
| WO | WO00/20860 | 10/1998 |
| WO | WO98/42864 | 10/1998 |
| WO | WO00/31538 | 11/1998 |
| WO | WO99/05261 | 2/1999 |
| WO | WO 99/47550 A | 9/1999 |
| WO | WO99/65519 | 12/1999 |
| WO | WO00/02904 | 1/2000 |
| WO | WO00/18805 | 4/2000 |
| WO | WO00/27625 | 5/2000 |
| WO | WO01/10437 A1 | 8/2000 |
| WO | WO00/63700 | 10/2000 |
| WO | WO00/75163 A1 | 12/2000 |
| WO | WO01/04157 A2 | 1/2001 |

OTHER PUBLICATIONS

Brassart et al. "Conformational Dependence of Collagenase (Matrix Metalloproteinase-1) Up-Regulation by Elastin Peptides in Cultured Fibroblasts", J Biol Chem, Nov. 17, 2000, PMID 11084020.

Stracke et al. "Biochemical Characterization of the Catalytic Domain of Human Matrix Metalloproteinase 19, Evidence of a Role as a Potent Basement Membrane Degrading Enzyme", J Biol Chem, May 19, 2000; 14809-16, 275 (20), PMID 10809722.

Olson et al. "Characterization of the Monomeric and Dimeric Forms of Latent and Active Matrix Metalloproteinase-9, Differential Rates of Activation by Stromelysin 1", J Biol Chem, Jan. 28, 2000, 2661-8, 275(4), PMID 10644727.

Fujise et al. Prognostic Impact of Cathepsin B and Matrix Metalloproteinase-9 in Pulmonary Adenocarcinomas by Immunohistochemical Study, Lung Cancer, Jan. 19-26, 2000, 27 (1), PMID 10672780.

Jones et al. "Expression of MMP-2 and MMP-9, Their Inhibitors, and the Activator MT1-MMP in Primary Breast Carcinomas", J Pathol, Oct. 16-18, 1999, 189(2), PMID 10547569.

Ambrose et al. "Detection System for Reaction-Rate Analysis in a Low-Volume Proteinase-Inhibition Assay", Anal Biochem, Oct. 15, 1998, 150-7, 263(2), PMID 9799526.

Hoyhtya et al. "Monoclonal Antibodies to Type IV Collagenase Recognize a Protein with Limited Sequence Homology to Interstitial Collagenase and Stromelysin", FEBS Lett, Jun. 6, 1988, 109-13, 233(1), PMID 2838321.

Nwomeh et al. "Dynamics of the Matrix Metalloproteinases MMP-1 and MMP-8 in Acute Open Human Dermal Wounds", Wound Repair Regen, Mar.-Apr. 1998, 127-34, 6(2), PMID 9776855.

Nielsen et al. "Expression of Matrix Metalloprotease-9 in Vascular Pericytes in Human Breast Cancer", Lab Invest, Oct. 1997, 345-55, 77(4), PMID 9354769.

Kodate et al. "Expression of Matrix Metalloproteinase (Gelatinase) in T1 Adenocarcinoma of the Lung", Pathol Int, Jul. 1997, 461-9, 47(7), PMID 97378788.

Itoh et al. Flow Injection Analysis for Measurement of Activity of Matrix Metalloproteinase-7 (MMP-7), J Pharm Biomed Anal, Jun. 1997, 1417-26, 15(9-10), PMID 9226571.

Verheijen et al. "Modified Proenzymes as Artificial Substrates for Proteolytic Enzymes: Colorimetric Assay of Bacterial Collagenase and Matrix Metalloproteinase Activity Using Modified Pro-Urokinase", Biochem J, May 1, 1997, 603-9, 323 (Pt 3)(3), PMID 9169591.

Sang et al. "Activation of Human Progelatinase A by Collagenase and Matrilysin: Activation of Procollagenase by Matrilysin", J Protein Chem, Apr. 1996, 243-53, 15(3), PMID 8804571.

Nagase, et al. "Human Matrix Metalloproteinase Specificity Studies Using Collagen Sequence-Based Synthetic Peptides", Biopolymers, 1996, 399-416, 40(4), PMID 8765610.

McGeehan et al. "Characterization of the Peptide Substrate Specificities of Interstitial Collagenase and 92kDa Gelatinase. Implications for Substrate Optimization", J Biol Chem, Dec. 30, 1994, 32814-20, 269(52), PMID 7806505.

Bickett et al. A High Throughput Fluorogenic Substrate for Stromelysin (MMP-3), Ann NY Acad Sci, Sep. 6, 1994, 351-5, 732, PMID 7978805.

Nagase et al. Design and Characterization of a Fluorogenic Substrate Selectively Hydrolyzed by Stromelysin 1 (Matrix Metalloproteinase-3), J Biol Chem, Aug. 19, 1994, 20952-7, 269(33), PMID 8063713.

Okazaki et al. "Gene Expression of MMPs and TIMPs in the Process of Hepatic Fibrosis" Nippon Rinsho, Feb. 1993, 428-34, 51(2), PMID 8464157.

Niedzwiecki et al. "Substrate Specificity of the Human Matrix Metalloproteinase Stromelysin and the Development of Continuous Fluorometric Assays", Biochemistry, Dec. 22, 1992, 12618-23, 31(50), PMID 1472498.

Harrison et al. "Mechanic Studies on the Human Matrix Metalloproteinase Stromelysin", Biochemistry, Nov. 10, 1992, 10757-62, 31(44), PMID 1420192.

Zucker et al. "Immunoassay of Type IV Collagenase/Gelatinase (MMP-2) in Human Plasma", J Immunol Methods, Apr. 8, 1992, 189-98, 148(1-2), PMID 1373424.

Clark et al. "Polyclonal Antibodies Against Human Fibroblast Collagenase and the Design of an Enzyme-Linked Immunosorbent Assay to Measure TIMP-Collagenase Complex", Matrix, Apr. 1992, 108-15, 12(2), PMID 1318493.

Knight et al. "A Novel Coumarin-Labelled Peptide for Sensitive Continuous Assays of the Matrix Metalloproteinases", FEBS Lett, Jan. 27, 1992, 263-6, 296(3), PMID 1537400.

Angelton et al. "Flourogenic Peptide Substrates Optimized for Five Human Matrix Metalloproteinases", Matrix Suppl, 1992, 89-90, 1, PMID 1480101.

Stack et al. "Application of N-Carboxyalkyl Peptides to the Inhibition and Affinity Purification of the Porcine Matrix Metalloproteinases Collagenase, Gelatinase, and Stromelysin", Arch biochem Biophsys, Sep. 1992, 393, 297(2), PMID 1654808.

Netzel-Arnett et al. "Continuously Recording Fluorescent Assays Optimized for Five Human Matrix Metalloproteinases", Anal Biochem, May 15, 1991, 86-92, 195(1).

Clark et al. "Polyclonal and Monoclonal Antibodies Against Human Tissue Inhibitor of Metalloproteinases (TIMP) and the Design of an Enzyme-Linked Immunosorbent Assay to Measure TIMP", Matrix, Apr. 1991 76-85, 11(2), PMID 1649376.

Brophy et al. "Tissue Inhibitor of Metalloproteases (TIMP) is Matrix Associated in Aortic Tissue: Report of a Radioimmunoassay", Biochem Biophys Res Commun, Mar. 30, 1990, 898-903, 167(3), PMID 2322285.

Teahan et al. "Substrate Specificity of Human Fibroblast Stromelysin. Hydrolysis of Substance P and its Analogues", Biochemistry, Oct. 17, 1989, 8497-501, 28(21), PMID 2481496.

Harrison et al. "A Semicontinuous, High-Performance Liquid Chromatography-Based Assay for Stromelysin", Anal Biochem, Jul. 1989, 110-3, 180(1), PMID 2479283.

Stetler-Stevenson et al. "The Activation of Human Type IV Collagenase Proenzyme. Sequence Identification of the Major Conversion Product Following Organomercurial Activation", J Biol Chem, Jan. 25, 1989, 264(3), 1353-6, PMID 2536363.

Maliszewska et al. "Development of an ultrasensitive enzyme immunoassay for the determination of matrix metalloproteinases-9 (MMP-9) levels in normal human cerebrospinal fluid", *J. Neuroimmunol.* (2001) : 116(2), 233-238. Chemical Abstracts, 7-Enzymes, vol. 135, No. 16., 135:223205.

Wang et al. "One-step sandwich enzyme immunoassay using monoclonal antibodies for detection of human enamelysin (MMP-20)", *Eur. J. Oral Sci.* (2000): 108(6), 530-537. Chemical Abstracts, 7-Enzymes, vol. 134, No. 11., 134:143641f.

Terstappen, et al. "Methods and reagents for the rapid and efficient isolation of circulating cancer cells using immunomagnetic enrichment combines with flow cytometric and immunocytochemical analysis", *Immunivest: University of Texas Soutwestern Medical Center/Dalls, USA*. PCT Int. Appl. WO99 41,613, Aug. 19, 1999, US Appl. PV110,202, Nov. 30 1998; pp. 115. Chemical Abstracts, 9-Biochemical Methods, vol. 131, No. 12, 1999, 131:155517w.

Baker et al. "Real-time monitoring of recombinant protein concentration in animal cell cultures using an optical biosensor", *Genet. Eng. Biotechnol.* (1997): 17(2&3), 69-74. Chemical Abstracts 16-Fermentation and Bioindustrial Chemistry, vol. 128, No. 6, 1998, 128:60742g.

Stivers, et al. "A miniaturized self-contained single-use disposable quantitative test for hemoglobin A1c in blood at the point of care", *Diabetes Technol Ther* (2000) Winter:2(4):517-26. PMID: 11469613.

Maliszewska et al. "Development of an ultrasensitive enzyme immunoassay for the determination of matrix metalloproteinases-9 (MMP-9) levels in normal human cerebrospinal fluid", *J Neuroimmunol* Jun. 1 2001:116(2):223-7. PMID: 11438179.

Wang et al. "One-step sandwich enzyme immunoassay using monoclonal antibodies for detection of human enamelysin (MMP-20)" *Eur J Oral Sci* Dec. 2000;108(6):530-7. PMID: 11153928.

Hanemaaijer et al. "Increased gelatinase0A and gelatinase-B activities in malignant vs. benign breast tumors", *Int J Cancer* Apr. 15, 2000;86(2):204-7. PMID: 10738247.

Stearns et al. "Evidence for increased activated metalloproteinases 2 (MMP-2a) expression associated with human prostate cancer progression" *Incol Res* (1996);8(2):69-75. PMID: 8859777.

Manicourt et al. "An assay for matrix metalloproteinases and other proteases acting on proteoglycans, casein, or gelatin" *Anal Biochem* Dec. 1993;215(2):171-9. PMID: 8122775.

Cooksley et al. "Immunoassays for the detection of human collagenase, stromelysin, tissue inhibitor of metalloproteinases (TIMP) and enzyme-inhibitor complexes" *Matrix* Oct. 1990;10(5):285-91. PMID: 1964712.

Hoffman et al. "Matrix Metalloproteinases in Human Melanoma" *The Journal of Investigative Dermatology, Inc.* (2000) pp. 337-344.

Trengove et al. "Analysis of the acute and chronic wound environments: the role of proteases and their inhibitors" *Wound Repair and Regeneration*, Nov.-Dec. 1999 pp. 442-452.

Vaalamo et al. "Differential Expression of Tissue Inhibitors of Metalloproteinases (TIMP-1, -2, -3, and -4) in Normal and Aberrant Wound Healing" *Human Pathology* vol. 30, No. 7 (Jul. 1999), pp. 795-802.-

Soo et al. "Differential Expression of Matrix Metalloproteinases and Their Tissue-Derived Inhibitors in Cutaneous Wound Repair" *Inhibitor Expression in Wound Repair, Plastic and Reconstruction Surgery* (Feb. 2000), pp. 638-647.

Saarialho-Kere, U.K. "Patterns of matrix metalloproteinases and TIMP expression in chronic ulcers" *Arch Dermatol Res* (1998) 290 (Suppl):S47-S54.

Herouy et al. "Matrix metalloproteinases and venous leg ulceration" *Eur J Dermatol* 2000; 9: 173-80.

Herouy et al. "Matrix metalloproteinases and venous leg ulceration" *Eur J Dermatol* vol. 10, Issue 3, Apr.-May 2000: 173-80, Review article.

Whittaker et al. "Matrix Metalloproteinases and their Inhibitors—Current Status and Future Challenges" *Celltransmissions*, vol. 17, No. 1, pp. 3-14, year?.

Zembower et al. "Novel Anthraquinone Inhibitors of Human Leukocyte Elastase and Cathepsin G" *J. Med. Chem.* 1992, 35, 1597-1605.

Brem et al. "Interstitial chemotherapy with drug polymer implants for the treatment of recurrent gliomas" *J Neurosurg* 1991 74:441-446.

Shaw et al. "Metalloproteinase inhibitors: new opportunities for the treatment of rheumatoid arthiritis and osteoarthritis" *Exp. Opin. Invest. Drugs* (2000) 9(7):1469-1478.

A.J.P. Docherty et al., "Sequence of Human Tissue Inhibitor of Metalloproteinase and Its Identity to Erythroid-potentiating activity," *Nature*, vol. 318, No. 7, pp. 66-69 (Nov. 17, 1985).

"Wound care is bound for an active future", *Clinica*, 559, (Jul. 7, 1993),14-17.

"Wound Healing—Focus on Growth Factors, Skin Substitutes", *MedPro Month*, 2(6), (Jun. 1992), 91-94.

Berg, J. M., et al., "Lessons from zinc-binding peptides", *Annu Rev Biophys Biomol Struct.*, 26, (1997), 357-71.

Browner, M. F., et al., "1MMQ", *NCBI Protein Database*, http://www.ncbi.nlm.nih.gov/entrez/viewer.fcgi?db=protein&val=1431761, (1995).

Butler, Georgina S., "The Specificity of TIMP-2 for Matrix Metalloproteinases Can Be Modified by Single Amino Acid Mutations", *Journal of Biological Chemistry*, 274 (29), (Jul. 16, 1999), 20391-20396.

Duivenvoorden, Wilhelmina C., "Use of Tetracycline as an Inhiitor of Matrix Metalloproteinase Activity Secreted by Human Bone-Metastasizing Cancer Cells", *Invasion Metastasis*, 17, (1997), 312-322.

Fernandez-Catalan, C., et al., "1BUV", *Protein Databank*, (Sep. 7, 1998).

Gomis-Ruth, F. X., "1UEA", *Protein Databank*, TIMP-1/MMP complex, 1UEA (Gomis-Ruth, Huang, Becker), (Jun. 6, 1997).

Gomis-Ruth, F. X., et al., "TIMP-1", *NCBI Protein Database*, (1997).

Grams, F., et al., "1JAO", *Protein Databank*, (Mar. 11, 1996).

Guex, Nicolas, "Swiss-MODEL and the Swiss-Pdb Viewer: An environment for comparative protein modeling", *Electrophesis*, 18, (1997), 2714-2723.

Hayward, Matthew M., "Convenient Syntheses of Bifunctional Metal Chelates", *Journal of Organic Chemistry*, 60(12), (Jun. 16, 1995), 3924-3927.

Levy, Daniel E., "Matrix Metalloproteinase Inhibitors: A Structure-Activity Study", *Journal of Medicinal Chemistry*, 41(2), (Jan. 15, 1998), 199-223.

Li, J., et al., "1FBL", *NCBI Protein Database*, http://www.ncbi.nlm.nih.gov/entrez/viewer.fcgi?db=protein&val=1310872, (1995).

Libson, A. M., et al., "1GEN", *NCBI Protein Database*, http://www.ncbi.nlm.nih.gov/entrez/viewer.fcgi?db=protein&val=1827787,(1995).

Meng, Qi, "Residue 2 of TIMP-1 is a major determinant of affinity and specificity for matrix metalloproteinases but effects of substitutions do not correlate with those of the corresponding P1' residue of substrate", *Journal of Biological Chemistry*, 274 (15), (1999),10184-10189.

Odake, Shinjiro, "Inhibition of matrix metalloproteinase by peptidyl hydroxamic acids", *Biochemical and Biophysical Research Communications*, 199 (3), (1994), 1442-1446.

Overall, Christopher M., "Identification of the tissue inhibitor of metalloproteinases-2 (TIMP-2) binding site on the hemopexin carboxyl domain of human gelatinase A by site-directed mutagenesis. The hierarchical role in binding TIMP-2 of the unique cationic clusters of hemopexin m", *Journal of Biological Chemistry*, 274 (7), (Feb. 12, 1999), 4421-4429.

Reinemer, P., et al., "1JAN", *Protein Databank*, (Mar. 11, 1996).

Sayle, Roger A., "RASMOL: biomolecular graphics for all", *Trends in Biochemical Sciences*, 20, (1995), 333-379.

Su, Jui-Lan, "Monoclonal Antibodies against Human Collagenase and Stromelysin", *Hybridoma*, 14 (4), (1995), 383-390.

Tuuttila, A., et al., "1BR9", *NCBI Protein Database*, (1998).

Wojtowicz-Praga, S. M., et al., "Matrix metalloproteinase inhibitors", *Investigational New Drugs*, 15(1), (1997), 61-75.

SEQUENCE LISTING

<160> NUMBER OF SEQ ID NOS: 10

<210> SEQ ID NO 1
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE

```
<222> LOCATION: (2)..(2)
<223> OTHER INFORMATION: X = Ser or Thr
<220> FEATURE:
<221> NAME/KEY: MISC_FEATURE
<222> LOCATION: (4)..(4)
<223> OTHER INFORMATION: X = Ser, Ala or Val

<400> SEQUENCE: 1

Cys Xaa Cys Xaa Pro His Pro
1               5

<210> SEQ ID NO 2
<211> LENGTH: 12
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X = Ile or Val
<220> FEATURE:
<221> NAME/KEY: MISC_FEATURE
<222> LOCATION: (2)..(2)
<223> OTHER INFORMATION: X = Glu, Gln or Arg
<220> FEATURE:
<221> NAME/KEY: MISC_FEATURE
<222> LOCATION: (3)..(3)
<223> OTHER INFORMATION: X = Phe or Tyr
<220> FEATURE:
<221> NAME/KEY: MISC_FEATURE
<222> LOCATION: (4)..(4)
<223> OTHER INFORMATION: X = Ile or Val
<220> FEATURE:
<221> NAME/KEY: MISC_FEATURE
<222> LOCATION: (5)..(5)
<223> OTHER INFORMATION: X = Tyr or His
<220> FEATURE:
<221> NAME/KEY: MISC_FEATURE
<222> LOCATION: (7)..(7)
<223> OTHER INFORMATION: X = Ala, Pro or Glu
<220> FEATURE:
<221> NAME/KEY: MISC_FEATURE
<222> LOCATION: (8)..(8)
<223> OTHER INFORMATION: X = Pro, Phe or Ala
<220> FEATURE:
<221> NAME/KEY: MISC_FEATURE
<222> LOCATION: (9)..(9)
<223> OTHER INFORMATION: X = Ser, Asp or Met
<220> FEATURE:
<221> NAME/KEY: MISC_FEATURE
<222> LOCATION: (10)..(10)
<223> OTHER INFORMATION: X = Ala or Ser
<220> FEATURE:
<221> NAME/KEY: MISC_FEATURE
<222> LOCATION: (11)..(11)
<223> OTHER INFORMATION: X = Val or Leu
<220> FEATURE:
<221> NAME/KEY: MISC_FEATURE
<222> LOCATION: (12)..(12)
<223> OTHER INFORMATION: X = Cys or Gly

<400> SEQUENCE: 2

Xaa Xaa Xaa Xaa Xaa Thr Xaa Xaa Xaa Xaa Xaa Xaa
1               5                   10

<210> SEQ ID NO 3
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
```

```
<223> OTHER INFORMATION: X = Met, Val or Leu
<220> FEATURE:
<221> NAME/KEY: MISC_FEATURE
<222> LOCATION: (2)..(2)
<223> OTHER INFORMATION: X = His, Phe or Tyr
<220> FEATURE:
<221> NAME/KEY: MISC_FEATURE
<222> LOCATION: (3)..(3)
<223> OTHER INFORMATION: X = Ile or Thr
<220> FEATURE:
<221> NAME/KEY: MISC_FEATURE
<222> LOCATION: (4)..(4)
<223> OTHER INFORMATION: X = Thr, His or Gly
<220> FEATURE:
<221> NAME/KEY: MISC_FEATURE
<222> LOCATION: (5)..(5)
<223> OTHER INFORMATION: X = Leu or Thr
<220> FEATURE:
<221> NAME/KEY: MISC_FEATURE
<222> LOCATION: (7)..(7)
<223> OTHER INFORMATION: X = Asp, Asn or Ser
<220> FEATURE:
<221> NAME/KEY: MISC_FEATURE
<222> LOCATION: (8)..(8)
<223> OTHER INFORMATION: X = Phe or Tyr
<220> FEATURE:
<221> NAME/KEY: MISC_FEATURE
<222> LOCATION: (9)..(9)
<223> OTHER INFORMATION: X = Ile or Val

<400> SEQUENCE: 3

Xaa Xaa Xaa Xaa Xaa Cys Xaa Xaa Xaa
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic peptide

<400> SEQUENCE: 4

Cys Ser Ala Val Pro Val His
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic peptide

<400> SEQUENCE: 5

Asp Ser Ala Val Pro Val His
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic peptide

<400> SEQUENCE: 6

Ile Tyr Thr Ala Cys Met Ser Ala Val
1               5

<210> SEQ ID NO 7
<211> LENGTH: 7
<212> TYPE: PRT
<213> ORGANISM: Artificial Sequence
```

```
<220> FEATURE:
<223> OTHER INFORMATION: Synthetic peptide

<400> SEQUENCE: 7

Val His Thr His Leu Cys Asp
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic peptide

<400> SEQUENCE: 8

Cys Thr Cys Val Pro
1               5

<210> SEQ ID NO 9
<211> LENGTH: 4
<212> TYPE: PRT
<213> ORGANISM: Artificial Sequence
<220> FEATURE:
<223> OTHER INFORMATION: Synthetic peptide

<400> SEQUENCE: 9

Cys Asp Ile Cys
1

<210> SEQ ID NO 10
<211> LENGTH: 5
<212> TYPE: PRT
<213> ORGANISM: Artificial Sequence
<220> FEATURE:
<223> OTHER INFORMATION: Synthetic peptide

<400> SEQUENCE: 10

His Thr Ile Thr His
1               5
```

DESIGN AND USE OF ADVANCED ZINC CHELATING PEPTIDES TO REGULATE MATRIX METALLOPROTEINASES

FIELD OF THE INVENTION

The present invention relates to compositions and methods for enhancing wound healing, especially chronic wounds (e.g., diabetic wounds, pressure sores). More specifically, the invention relates to improved wound healing through regulation of matrix metalloproteinase activity.

BACKGROUND OF THE INVENTION

In normal tissues, cellular connective tissue synthesis is offset by extracellular matrix degradation, the two opposing effects existing in dynamic equilibrium. Degradation of the matrix is brought about by the action of matrix metalloproteinases (MMPs) released from resident connective tissue cells and invading inflammatory cells. Normally, these catabolic enzymes are tightly regulated at the level of their synthesis and secretion and also at the level of their extracellular activity. Extracellular control occurs primarily by regulation with specific enzymes, such as TIMPs (tissue inhibitors of metalloproteinases), which form complexes with MMPs. These complexes prevent MMP action. Cellular level control of MMP activity occurs primarily by regulating MMP gene expression and down regulating the expression of the membrane bound MMPs (MT-MMP) that activate the excreted proenzyme form of the MMP.

MMPs are a family of neutral metalloenzymes capable of degrading extracellualr matrix (ECM) macromolecules. Members of this family that have been isolated and characterized include interstitial fibroblast collagenase, stromelysin, and type IV collagenase. Other potential members include a poorly characterized 94,000 dalton gelatinase and several low molecular weight gelatinases and telopeptidases. Structurally, MMPs contain a zinc(II) ionic site at the active site of the protein. Binding of zinc to the ionic site is required for hydrolytic activity.

TIMPs are glycoproteins that specifically regulate interstitial collagenase on a 1:1 stoichiometric basis. That is, TIMPs form very specific regulatory complexes with MMPs, only regulating a specific subset of the MMPs. No naturally occurring TIMP molecule singly regulates all types of MMPs.

In chronic wounds, the ratio of MMPs to TIMPs is high, such that most of the MMPs are unregulated. This unregulated MMP activity results in the accelerated, uncontrolled breakdown of the ECM, leading to destruction of the newly formed wound bed. Additionally, the concomitant elevation of proteinase levels, cause hydrolyzation of TIMP molecules, further increasing the MMP to TIMP ratio.

Many individuals suffer from chronic wounds. Open cutaneous wounds represent one major category of such wounds and include burn wounds, neuropathic ulcers, pressure sores, venous stasis ulcers, and diabetic ulcers. Worldwide, eight million people have chronic leg ulcers and seven million people have pressure sores (Clinica 559, 14–17, 1993). In the U.S. alone, the prevalence of skin ulcers is 4.5 million, including two million pressure sore patients, 900,000 venous ulcer patients and 1.6 million diabetic ulcer patients (Med Pro Month, June 1992, 91–94). The cost involved in treating these wounds is staggering and, at an average of $3,000 per patient, reaches over $13 billion per year for the U.S. alone.

Burn wounds have a reported incidence of 7.8 million cases per year worldwide, 0.8 million of which need hospitalization (Clinica 559). In the U.S., there are 2.5 million burn patients per year, 100,000 of which need hospitalization and 20,000 of which have burns involving more than 20% of the total body surface area (MedPro Month, June 1992).

Many other problems also result from the uncontrolled breakdown of connective tissues by MMPs. These problems include, for example, rheumatoid arthritis; osteoarthritis; osteopenias, such as osteoporosis, periodontitis, gingivitis, corneal epidermal, and gastric ulceration; tumour metastasis, invasion, and growth; neuroinflammatory disorders, including those involving myelin degradation, for example, multiple sclerosis; and angiogenesis dependent diseases, which include angiofibromas, hemangioma, solid tumors, blood-borne tumors, leukemia, metastasis, telangiectasia, psoriasis, scleroderma, pyogenic granuloma, myocardial angiogenesis, plaque neovascularization, coronary collaterals, ischemic limb angiogenesis, corneal diseases, rubeosis, neovascular glaucoma, diabetic retinopathy, retrolental fibroplasia, arthritis, diabetic neovascularization, macular degeneration, wound healing, peptic ulcer, fractures, keloids, vasculogenesis, hematopoiesis, ovulation, menstruation, and placentation.

Given the large number of diseases associated with MMP activity, there is a need to control MMP activity. Several approaches have been suggested to accomplish such regulation. One approach has focused on the catalytic role of zinc in MMPs, and designing zinc chelating regulators. Potent regulators have been generated by introducing zinc chelating groups, such as peptide hydroxamates and thiol-containing peptides, into substrates. Peptide hydroxamates and TIMPs have been successfully used in animal models to treat cancer and inflammation. While these hydroxamates are potent as regulators of MMPs by binding to zinc, they are toxic to humans because they bind to all zinc-containing enzymes. Because many biochemical reactions occurring in the body require zinc, use of the hydroxamates detrimentally effects these other functions and can result in death.

Other known zinc-chelating MMP regulators are peptide derivatives based on naturally occurring amino acids and are analogues of the cleavage site in the collagen molecule (Odake et al. (1994) Biophys. Res. Comm. 199, 1442–46). Some MMP regulators are less peptidic in structure and may more properly be viewed as pseudopeptides or peptide mimetics. Such compounds usually have a functional group capable of binding to the zinc (II) bound in the MMP. Known compounds include those in which the zinc binding group is a hydroxamic acid, carboxylic acid, sulphydryl, or oxygenated phosphorus (for example, phosphinic acid and phosphonamidate, including aminophosphonic acid) groups.

Other approaches include small molecule regulation (Levy et al. (1998) J. Med. Chem. 41, 199–223; Wojtowicz-Pragaet al. (1997) Invest. New Drugs 15, 61–75; Duivenvoorden, et al. (1997) Invasion and Metas. 17, 312–22) and regulation via anti-MMP antibodies (Su et al. (1995) Hybridoma. 14, 383–90).

More specifically, an elastase inhibitor is disclosed in U.S. Pat. No. 5,734,014 to Ishima et al. Elastase secreted by neutrophils causes tissue damage, and in this process, creates an active abundance of oxygen. Elafin isolated from psoriatics has elastase inhibiting activity. However, this naturally occurring elafin is unstable to oxidation. Ishima developed elafin derivatives that are stable to oxidation so that elastase regulation can be more efficient. The oxidation-stable derivative is created by partly modifying the amino acid sequence of natural elafin. The modification can be created by either chemical synthesis or site-directed mutagenesis.

U.S. Pat. No. 5,464,822 to Christophers et al. discloses a polypeptide that possesses inhibitory activity against human leukocyte elastase. The polypeptides possess inhibitory activity that is specific for serine proteases. For example, they possess inhibitory activity against proteases, such as human leukocyte elastase and porcine pancreatic elastase, but do not possess any significant inhibitory activity against trypsin. These polypeptides can be prepared by genetic engineering or obtained from psoriatic scales of human skin.

U.S. Pat. No. 5,698,671 to Stetler-Stevenson et al. discloses a protein defined by the presence of specific cysteine-containing amino acid sequences, isolated from the conditioned media of cultured human tumor cells, that binds with high affinity to MMPs and analogs thereof. The particular inhibitor is made by preparing peptides and proteins having a cysteine residue at the same interval as that of the various tissue inhibitors of metalloproteinase (TIMPs). The peptides must have at least two appropriately spaced cysteines to ensure inhibitory activity by virtue of a disulfide bridge formation. In addition, the invention discloses a method for purifying natural MMP inhibitors by MMP affinity chromatography.

Despite these varied approaches, the current art does not selectively regulate MMP activity. Traditionally, high affinity regulators have been utilized, resulting in complete MMP inhibition. However, shutting off all MMP activity is actually deleterious to the healing process, as some MMP activity is required for tissue remodelling. For example, potent inhibition aimed at binding the zinc (II) site is toxic to humans because it shuts off bind to all zinc-containing enzymes. It is therefore necessary to have regulation be selective.

Thus, there is a need in the art for improved regulation of MMPs to promote healing of chronic and acute wounds.

There is also a need in the art for an inhibitor having relatively good affinity, which is selective.

Furthermore, there is a need in the art for MMP inhibitors that are not toxic to the individual to whom they are administered.

SUMMARY OF THE INVENTION

Using a novel approach to wound site proteinase management, the present invention, in one aspect, provides a new class of MMP regulators. These regulators comprise a zinc chelator covalently attached to a peptide that corresponds to a region of a TIMP protein that directly interacts with an MMP molecule in the vicinity of the catalytic zinc molecule to bind wound site proteinases The binding specificity of the peptide will bring the zinc chelator into molecular proximity of the MMP bound zinc in such a way as to allow ligation. In addition to this affinity, the exact sequence of the peptide will allow targeting of specific MMPs. This chemistry regulates the level of MMP activity to a point that promotes healing. This provides a MMP regulator which can, with high affinity, selectively regulate MMP activity unlike known MMP regulators.

In another aspect, the present invention provides a method for making the new class of MMP regulators. The method comprises binding a zinc chelator to synthetic peptides. The peptide sequences chosen were the part of the TIMP that made the closest approach to the MMP in the vicinity of the catalytic zinc. The sequence is a common structural feature of the binding interface.

In yet another aspect, the present invention provides methods of treating chronic and/or acute skin wounds and other diseases in which MMPs play a role. These methods are advantageous over conventional methods in that they provide both improved selectivity and improved affinity. Additionally, the methods of the present invention provide selective binding to MMPs without causing potential harm to the individual being treated. This is accomplished through the use of novel MMP regulators including a zinc chelator attached to a TIMP derived peptide. These compositions are particularly effective at bind MMP without compromising other zinc-dependent biochemical activities. Finally, by applying these novel MMP regulators to an area to be treated, the present invention provides a method of controlling diseases cause by uncontrolled MMP activity without the use of toxic inhibitors.

Therefore, it is an object of the invention to provide new MMP regulators.

It is another object of the invention to provide MMP regulators that comprises a zinc chelator and synthetic peptides containing novel amino acid sequences that bind to the TIMP binding region of the MMP.

It is yet another object of the invention to provide novel synthetic peptides for use in the production of the MMP regulators of the invention.

It is a further object of the present invention to provide a novel zinc chelator for use in the production of the MMP regulators of the invention.

It is an object of the invention to provide synthetic peptides having SEQ ID Nos. 1, 2, and 3.

It is another object of the present invention to provide MMP regulators comprising peptides having SEQ ID Nos. 1, 2, or 3 and a zinc chelator.

It is yet another object of the invention to provide methods for treating chronic and acute wounds.

It is a further object of the present invention to provide methods for treating angiogenic-associated diseases.

DETAILED DESCRIPTION OF THE PREFERRED EMBODIMENTS

Figure 1:
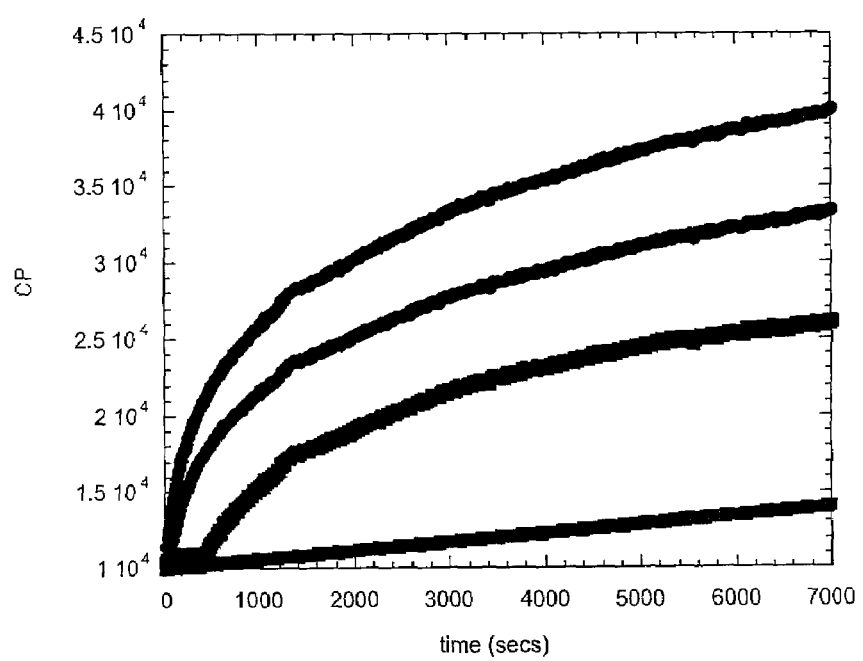
FIG. 1 illustrates a time course reaction of MMP-9 hydrolysis of fluoresceinated collagen in the presence of increasing amounts of the zinc chelating peptide. The curves (from top to bottom) represent MMP-9:ChePep-1 molar stoichiometries of 1:0, 1:0.25, 1:0.5, and 1:1. ChePep-1 is composed of PSDE coupled with the peptide having SEQ ID No. 4. The graph shows fluorescence as a function of time in the continuous assay.

MMPs contain a zinc molecule located in the active site. This zinc molecule intimately participates in the chemistry of degrading collagen. As a result, if the zinc is blocked or removed, enzymatic activity of the MMP can be inhibited. The present invention provides compositions (referred to herein as ChePeps) for the regulation of MMP activity. These compositions comprise a zinc chelator that is covalently attached to a TIMP-derived peptide. The zinc chelator is any compound that binds zinc, whether or not the molecule is a true chelator. The TIMP-derived peptide corresponds to a region of the TIMP protein that directly interacts with the MMP molecule in the vicinity of the catalytic zinc molecule. The binding specificity of this peptide assists in bringing the zinc chelator into molecular proximity with the MMP bound zinc in such a way as to allow ligation of the zinc from the MMP. In addition to this affinity, the exact sequence of the peptide will allow targeting of specific MMPs. This chemistry regulates the level of MMP activity to a point that promotes healing.

Preferably, modern molecular modeling methodologies are employed to design the novel peptides of the present invention that can bind to the zinc (II) site of MMPs and, therefore, regulate a broad range of MMPs. Analysis of the three-dimensional structure of the various MMPs and TIMPs, and the chemical nature and identification of conserved and variant amino acids in the MMP-TIMP contact interface, is preferably accomplished through molecular modeling utilizing two visualization programs, Swiss PDB Viewer (Guex and Peitsch, 1997) and Rasmol (Sayle and Milner-White, 1995). The present inventors have found through visualization of TIMP-MMP complexes that the TIMP molecules make significant contact with the area surrounding the MMP active site.

Other investigators have explored the interaction between MMPs and TIMPs. (Butler et al. (1999) J. Biol. Chem. 274, 20391–96; Overall et al (1999) J. Biol. Chem. 274, 4421–29; Menget al. (1999) J. Biol. Chem. 274, 10184–89). In one embodiment, the present invention comprises derivation of peptides from TIMP proteins that comprise structures in accordance with the three regions of the TIMP proteins that are in close proximity to the MMP catalytic zinc.

In another embodiment, the novel synthetic peptides of the present invention comprise relatively short stretches of amino acids that correspond to the TIMP/MMP binding domain. These peptides can be coupled to a zinc chelator and are capable of binding many MMP enzymes in the region of the catalytic zinc.

In a preferred embodiment, the present invention comprises three peptides derived from TIMP regions that have a large number of specific side chain interactions with MMPs. The exact sequence of the peptide employed allows targeting of specific MMPs. These sequences are derived from three separate regions of TIMPs I–IV that contact MMPs.

These preferred peptides comprise the amino acid sequences designated as SEQ ID Nos. 1–3. These sequences are shown in Table 1 below. The peptide having SEQ ID No. 1 spans MMP amino acids 2–9. These peptides are seven amino acids in length. The peptide having SEQ ID No. 2 spans MMP amino acids 62–73 and is 12 amino acids in length. The peptide having SEQ ID No. 3 is 9 amino acids in length encompasses MMP residues 97–105.

Within these preferred peptides, there is a large degree of sequence variation, as denoted by positions in parentheses. This variability can be used as a tool to modulate binding affinity and specificity of TIMP binding interactions. The exact sequence of the peptide can be altered to modulate binding affinity and/or specificity, so long as there is a single cysteine residue in the peptide. These three preferred peptides can be further modified by C-ter amidation and N-ter acetylation. This charge neutralization is often found to increase binding affinity as it mimics the peptide being in the context of a whole protein. In sum, these specific peptides allow for altering the level of specific MMPs in a coordinated manner.

TABLE 1

| Peptide Family Sequences | |
| --- | --- |
| SEQ ID No. 1 | C-(S/T)-C-(S/A/V)-P-H-P |
| SEQ ID No. 2 | (I/V)-(E/Q/R)-(F/Y)-(I/V)-(Y/H)-T-(A/P/E)-(P/F/A)-(S/D/M)-(A/S)-(V/L)-(C/G) |
| SEQ ID No. 3 | (M/V/L)-(H/F/Y)-(I/T)-(T/H/G)-(L/T)-C-(D/N/S)-(F/Y)-(I/V) |

While not wishing to be bound by the following theory, it appears that the preferred ChePep complexes block the imino carboxylate groups via zinc chelation prior to activating the remaining carboxyl group for coupling to the peptides. Once liganded to the zinc ion, these carboxyl groups are not able to participate in the activation reaction. The zinc binding affinity is high enough to ensure a slow off rate, so that the liganding carboxyls are bound to the zinc throughout the NHS/EDC reaction. (See examples) The zinc ion is then removed by extensive dialysis. For example, the material can be dialyzed through a 500 MWCO cellulose acetate dialysis tube against 50% phosphate buffered saline (PBS)/water, preferably at room temperature for 48 hours.

In a preferred embodiment, the zinc chelator is a molecule that contains a diacetic acid moiety and thus, a good chelator of certain divalent cations, including zinc. Although these compounds are preferred, any small organic molecule that has the ability to ligand or chelate a zinc molecule can sterically access the MMP active site (without making any deleterious electrostatic interactions) is capable of incorporation into a chelating peptide (ChePep). The chelation process itself is not specific, in that any zinc is potentially a chelation target. Possible chelators include, but are not limited to, EDTA, EGTA, DTPA, CDTA, HEDTA, NTA, citric acid, salicylic acid, and malic acid. Other chelators include peptides that can bind zinc. For example, peptides SEQ ID No. 9 (CDIC) or SEQ ID No. 10 (HTITH) chelate the zinc moiety through interactions with the two cysteines (SEQ ID No. 9) or the two histidines (SEQ ID No. 10). These sequences are derived from the consensus structure of the zinc finger motif described by Berg (Berg et al., Ann Rev Biophys Biomol Struct, 1997, 26: 357–71. These peptides can be coupled to the targeting peptide via standard peptide synthesis.

In a preferred embodiment, one of three zinc chelating molecules is covalently attached to one of the several TIMP derived peptides that comprise the present invention. The chemical structures of these three zinc chelating molecules: pyridine disulfide ethylenediaminetetraacetic acid (PSDE), amino-iminodiacetic acid (IDA), and 2-amino-4-fluorophenol N,N,O triacetic acid (AFTA), are depicted below in Structure 1.

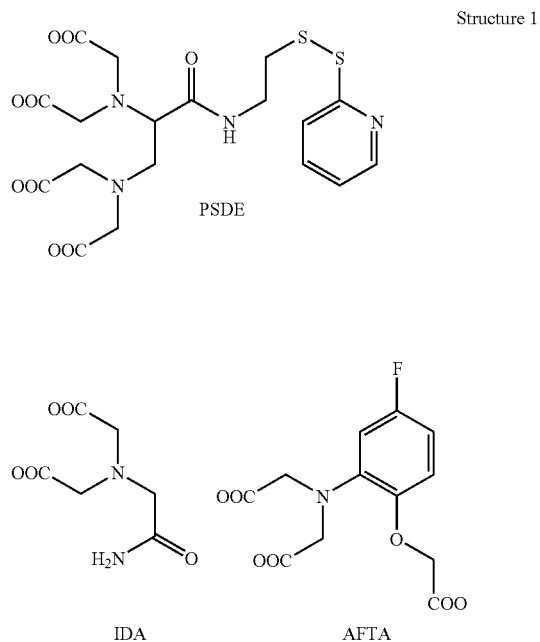

IDA   AFTA

Pyridine disulfide ethylenediaminetetraacetic acid (PSDE) of the present invention is produced in a literature synthesis. (Hayward et al (1995), J. Org. Chem. 60, 3924–27) Covalent coupling of PDSE to the peptide is carried out by a simple stoichiometric disulfide exchange with a cysteine at the amino terminus. Typically the process results in a substantially pure product with an overall yield of about 10–25 percent.

The peptide sequence shown in Structure 2 below is a modification of SEQ ID No. 1 wherein the cysteine in position 3 is replaced with an alanine. This molecule can be directly coupled to any free thiol via a simple disulfide exchange reaction.

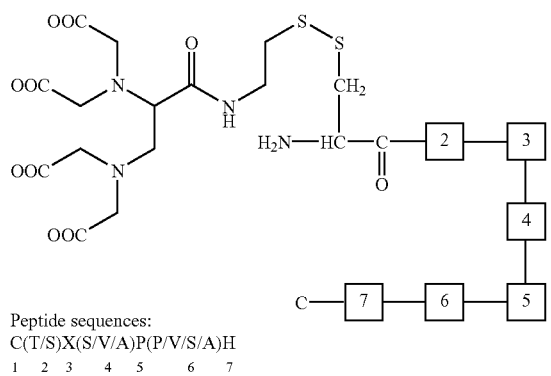

Peptide sequences:
C(T/S)X(S/V/A)P(P/V/S/A)H
1  2  3  4  5  6  7

In another embodiment, the present invention provides PSDE be coupled to SEQ ID No. 4 (CSAVPVH) with an overall yield of 80 percent. The reaction product is then purified via RP-HPLC as described in the Example. Introduction of this molecule, ChePep-1, to MMP-9 prevents the enzyme from degrading fluoresceinated collagen in a dose dependent manner as is shown in FIG. 1.

Figure 8:
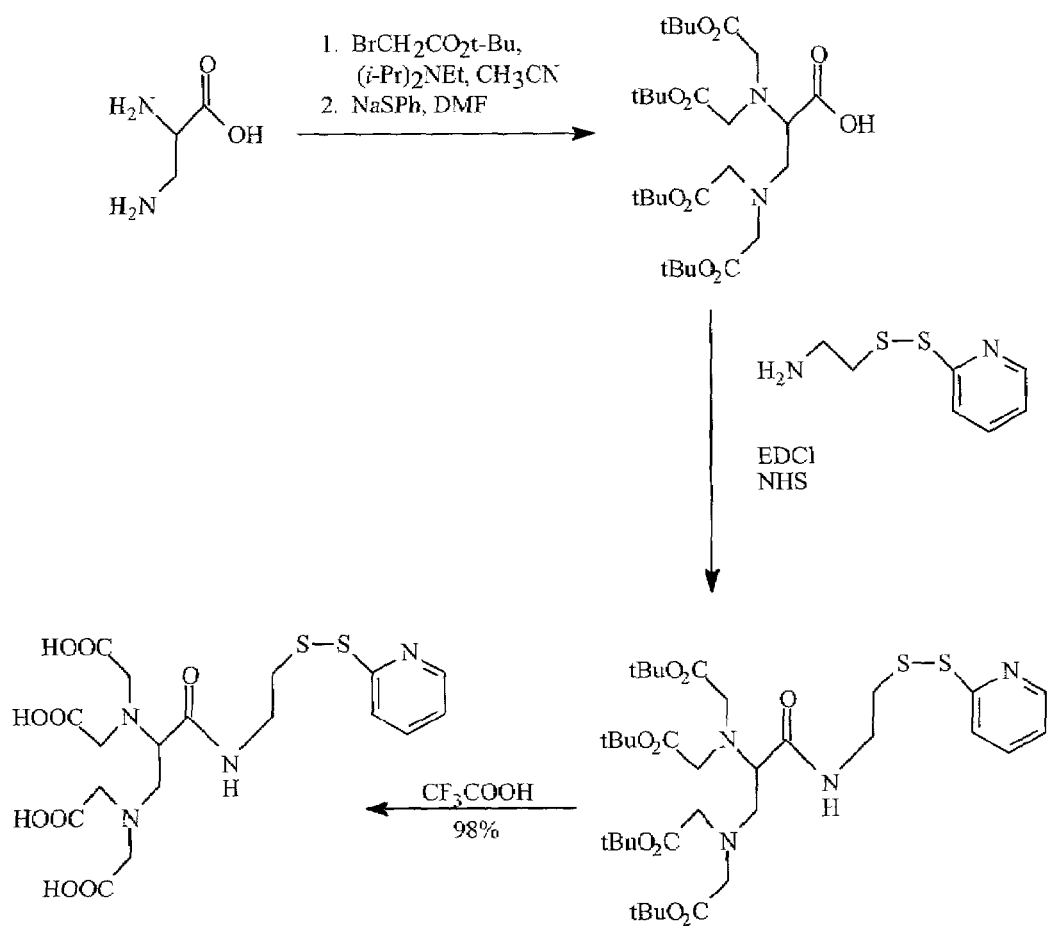
FIG. 8 is a reaction scheme for modification of EDTA to PSDE to allow coupling of the EDTA chelator to the peptides of the invention.

In yet another embodiment, the present invention provides creation of a combined regulator (binding specificity via the peptide and zinc chelation via the small molecule) by covalently joining EDTA or IDA to a TIMP derived peptide sequence. Ethylenediaminetetraacetic acid (EDTA) and iminodiacetic acid (IDA) are potent chelators of zinc. However, an EDTA chelator needs some prior literature synthesis in order to perform a coupling reaction preferred by the present invention. This synthesis is described by Hayward et al. (J. Org. Chem., Vol 60(12), 1995, 3924–3927) and is presented in FIG. 8. Such synthesis is not required for IDA because it is relatively easy to couple IDA to the carboxylate group of an aspartate that has been converted into a succinimide ester upon reaction with N-hydroxysuccinimide (NHS)/N-ethyl-N'-(dimethylaminopropyl)carbo-diimide (EDC) (EDC/NHS).

By coupling IDA to a similar peptide, SEQ ID No. 5 (DSAVPVH), the effect of the size of the EDTA moiety on ChePep-1 (PSDE and SEQ ID No.4) can be determined. In this instance, the carboxylate group of the N-ter peptide aspartic acid is activated to a succinimide ester via incubation with EDC/NHS. This straightforward reaction is commonly used to link free amino groups with activated carboxylates. The general structure of a peptide that is covalently coupled to IDA through an activated aspartic acid carboxylate is shown below in Structure 3.

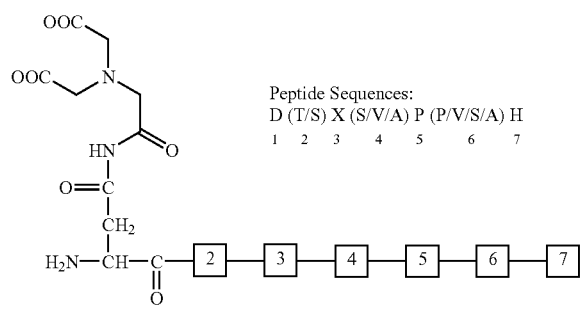

Structure 3

Peptide Sequences:
D (T/S) X (S/V/A) P (P/V/S/A) H
1  2    3  4      5  6        7

Preferably, the entire synthetic scheme that couples IDA to the peptide and purifies the final product proceeds with an overall 49 percent yield. To avoid possible contaminants in the reaction, use a peptide with a C-ter amide group. Hence the only free carboxyl group in the peptide should be the aspartic acid side chain.

Figure 2:
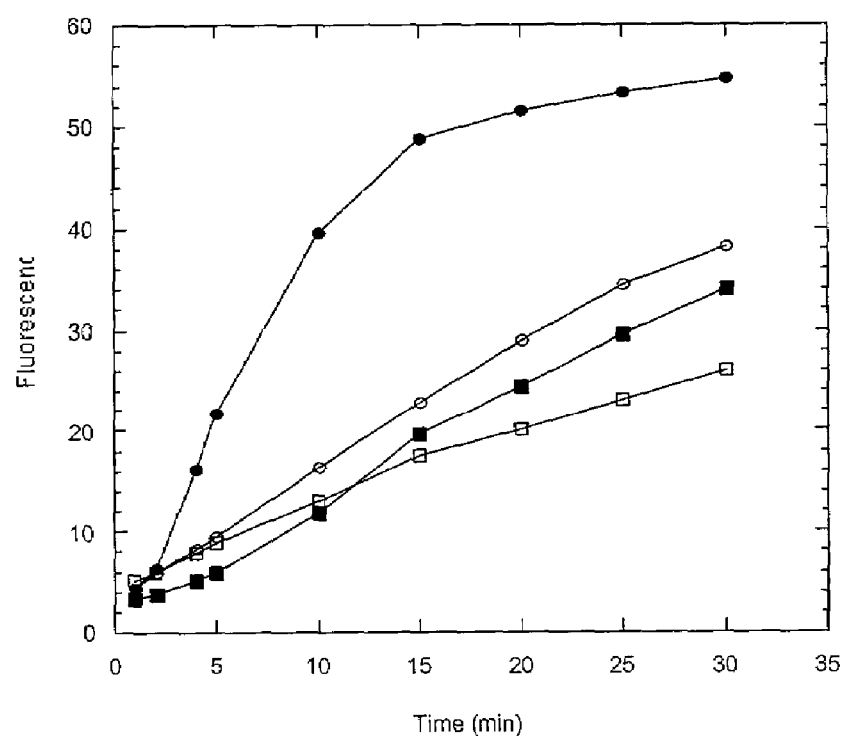
FIG. 2 depicts ChePep-2 regulation of MMP-9 via FRET assay. ChePep-2 is composed of IDA coupled with a peptide having Seq ID No. 5. This mixture was added to the FRET substrate peptide in reaction buffer. Fluorescence measurements were made at the indicated times. The curves represent ChePep-2: MMP-9 molar stoichiometries of 0:1 (closed circles), 0.1:1 (open circles), 0.2:1 (closed squares), 0.3;1 (open squares).

The molecule ChePep-2 (IDA and SEQ ID No. 5) regulates MMP-9 in the fluorescence resonance energy transfer (FRET) assay in a dose dependent manner. The construct is significantly more effective in regulating MMP-9 than was ChepPep-1, as demonstrated in FIG. 2. This may be due to the ability of an IDA moiety to more effectively ligate the active site zinc than PSDE because of stearic considerations as well as the need to satisfy charge interactions with the second chelating group on PSDE. In addition, the neutralization of the C-ter negative charge on the peptide via the amidation may also alter binding affinity.

In another embodiment, PSDE is coupled to a peptide of SEQ ID No. 2. Specifically, PSDE is coupled to a peptide having SEQ ID No. 10 that is aminated at the amino terminus (IYTACMSAV-NH$_2$) via the same disulfide exchange reaction previously discussed. The yield for the final product was 37%. The generalized structure of a chelating peptide (ChePep) composed of PSDE and SEQ ID No. 2 is shown below.

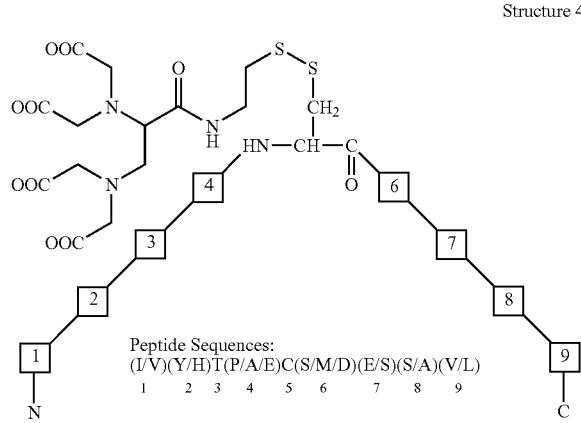

Structure 4

Peptide Sequences:
(I/V)(Y/H)T(P/A/E)C(S/M/D)(E/S)(S/A)(V/L)
1    2    3 4      5 6      7    8    9

If the cysteine residue in the fifth position of the above molecule is altered to aspartic acid, then IDA can be incorporated into the structure at the same position. In a preferred embodiment, IDA is coupled to SEQ ID No. 2, specifically, the peptide of SEQ ID No. 11 via the EDC/NHS reaction described in the Examples section. The final product yield was 75 percent. RP-HPLC chromatograms of both ChePep molecules revealed a single 214 nm absorbing peak.

Figure 3:
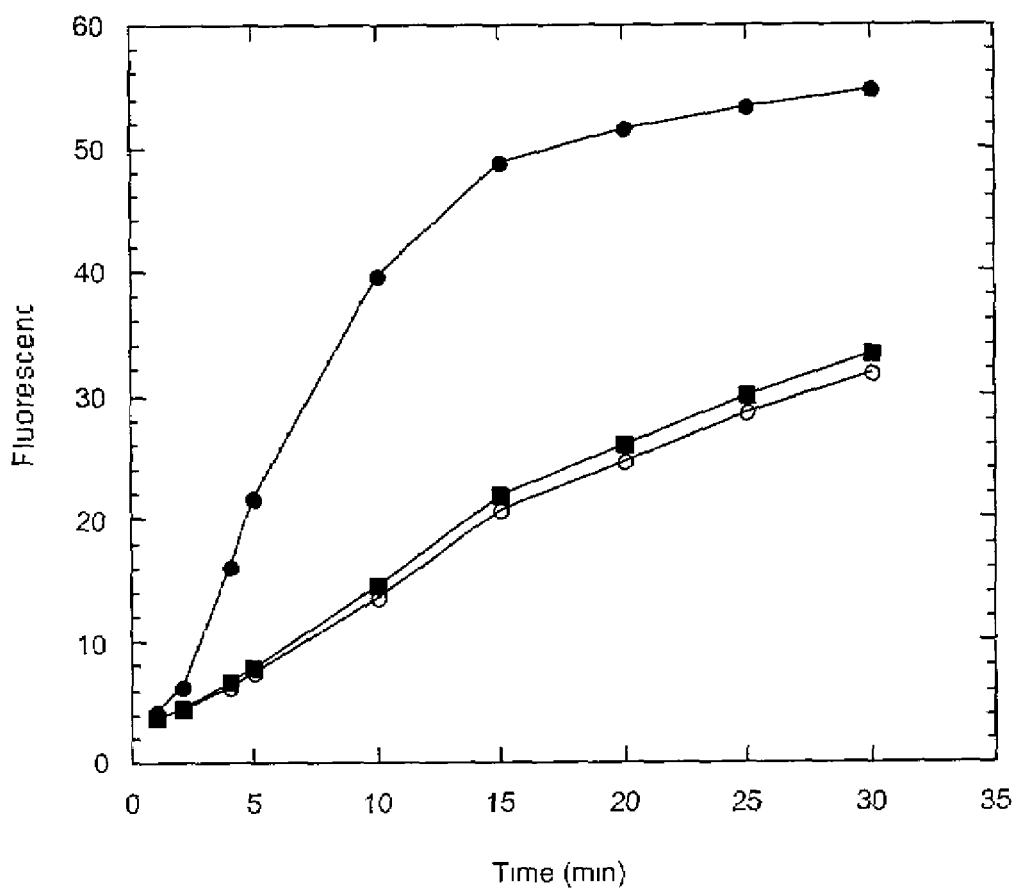
FIG. 3 represents ChePep-3 (closed squares) and ChePep-4 (open circles) regulation of MMP-9 via FRET assay. ChePep- 3 is made by combining PSDE with a peptide having SEQ ID No. 6 and ChePep-4 is made by combining IDA with a peptide having SEQ ID No. 6. ChePeps were incubated with MMP-9 for 10 minutes to effect binding. This mixture was added to the FRET substrate peptide in reaction buffer. Fluorescence measurements were made at the indicated times. MMP-9 only control is shown for reference (closed circles). ChePep:MMP-9 molar stoichiometry is 0.25:1.

Both ChePep-3 (PSDE and SEQ ID No. 6) and ChePep-4 (IDA and SEQ ID No. 6) show nearly identical ability to regulate MMP-9 in the standard FRET assay. The time dependent regulation course is displayed in FIG. 3. Despite the fact that there are differences between IDA and PSDE, molecular modeling indicates that the chelating groups of both ChePep constructs have similar accessibility to the MMP active site zinc. In fact, the second chelating group of PSDE does not make any energetically unfavorable interactions that would lower binding affinity. It is believed that ChePep-3 may gain some binding energy by the interaction of the carboxylate oxygen on the free liganding moiety with a MMP-9 backbone amide.

Molecules like 2-amino-4-fluorophenol N,N,O triacetic acid (AFTA) are not, according to scientific literature, generally known or used as metal chelators, but can in fact readily chelate zinc in this application. AFTA is found to bind well into the active site of MMP-like enzymes. The diacetate group off the 2 ring position chelates the zinc. The third acetate group can be used to couple a peptide to the molecule. The electronegative fluorine may also contribute to MMP regulation by making specific interactions in the enzyme active site. The general structure of SEQ ID No. 3 covalently linked to AFTA is depicted below.

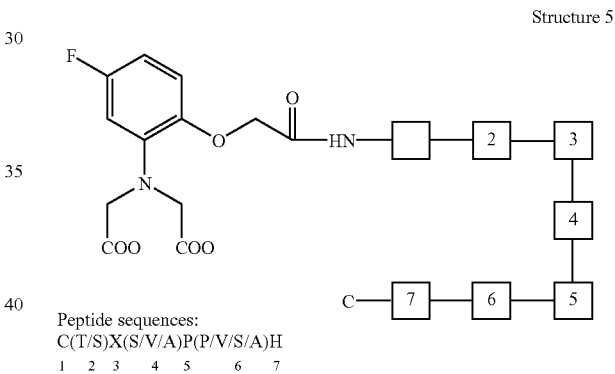

Structure 5

Peptide sequences:
C(T/S)X(S/V/A)P(P/V/S/A)H
1  2   3  4    5  6      7

The above structure is created by coupling a peptide having SEQ ID No. 7 (VHTHLCD) to an AFTA zinc chelator using the same EDC/NHS chemistry previously described, except that the activated carboxyl group was donated by the AFTA moiety. Since there are three free carboxyl groups found on AFTA, only two of which can participate in zinc ligation (see Structure 1), it is necessary to make those chelating groups unreactive to EDC/NHS treatment. This can be accomplished by mixing AFTA with zinc sulfate prior to EDC/NHS activation. The zinc ion is chelated by the iminodiacetic acid moiety, leaving a single free carboxylate. The succinimide ester is then formed on this group as described in the Examples section. The activated AFTA-zinc complex is coupled to the N-ter amino group of the peptide, and the resulting molecule (ChePep-5) is purified to homogeneity by RP-Phase HPLC. Preferably, the total recovery yield was 61% and the final material is judged to be 97% pure. The generalized structure of this type of regulator, shown in Structure 5, is capable of preventing the hydrolysis of the FRET peptide in a dose dependent manner.

Figure 4:
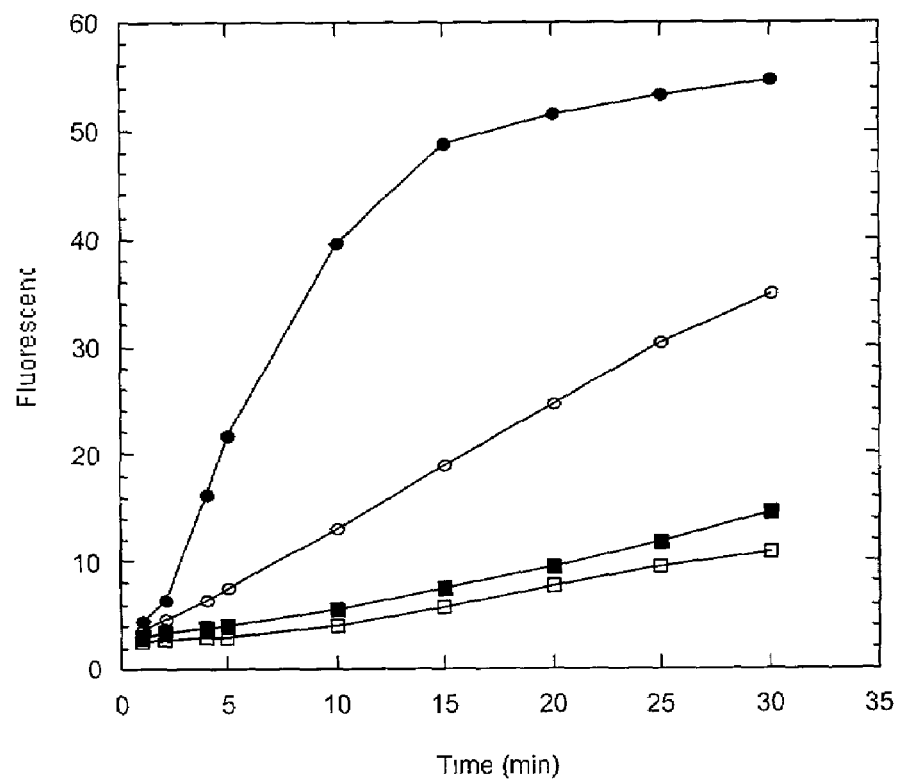
FIG. 4 illustrates ChePep-5 regulation of MMP-9 via FRET assay. ChePep-5 is composed of a AFTA combined with a peptide having SEQ ID No. 7. ChePep-5 was incubated with MP-9 for 10 minutes to effect binding. This mixture was added to the FRET substrate peptide in reaction buffer. Fluorescence measurements were made at the indicated times. The curves represent ChepPep-5: MMP-9 molar stoichiometries of 0:1 (closed circles), 0.1:1 (open circles), 0.2:1 (closed squares), 0.3:1 (open squares). Excitation was at 365 nm, and the emission was fixed at 450 nm.

In fact, according to the molar stoichiometries test depicted in FIG. 4, ChePep-5 proves to be a better regulator than the IDA or the PSDE based chelating peptides. Its success can be attributed to, but not limited to, four factors: the fluorine group which, because of its electron negativity, tenaciously binds to proteins; the ring itself, being hydrophobic, binds well to the hydrophobic active site of the MMP; the presence of three carboxyl groups to bind to allow for zinc chelation; and the amino groups to create specificity.

In another embodiment of this invention, a second AFTA peptide construct is synthesized. This peptide (ChePep-6) comprises SEQ ID No. 8 (CTCVP) and an AFTA, with the AFTA molecule coupled to the peptide amino terminus. Coupling is preferably performed by first mixing an equal amount of zinc sulfate and AFTA. The resulting complex is then activated with NHS/EDC. An amide coupling is then performed using the N-ter region of the peptide. Alternatively, AFTA can be linked to the cysteine thiol via a disulfide exchange reaction. The structure of the preferred chelating peptide is shown in Structure 6 below.

Structure 6

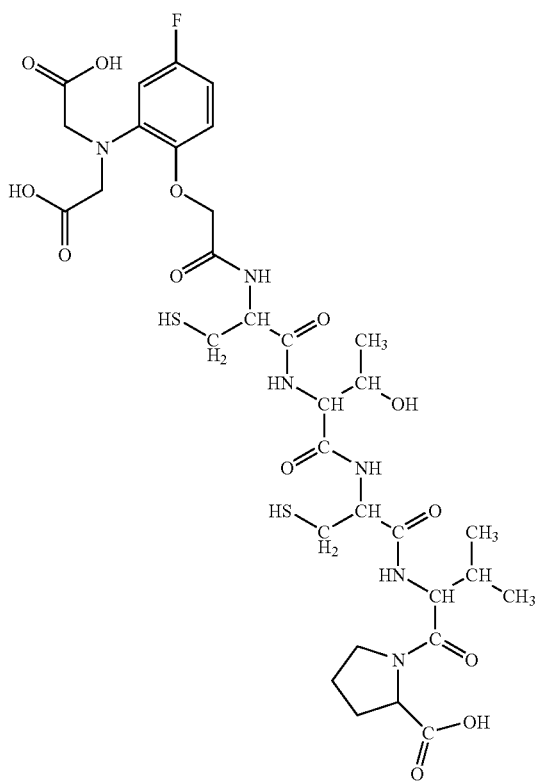

Figure 5:
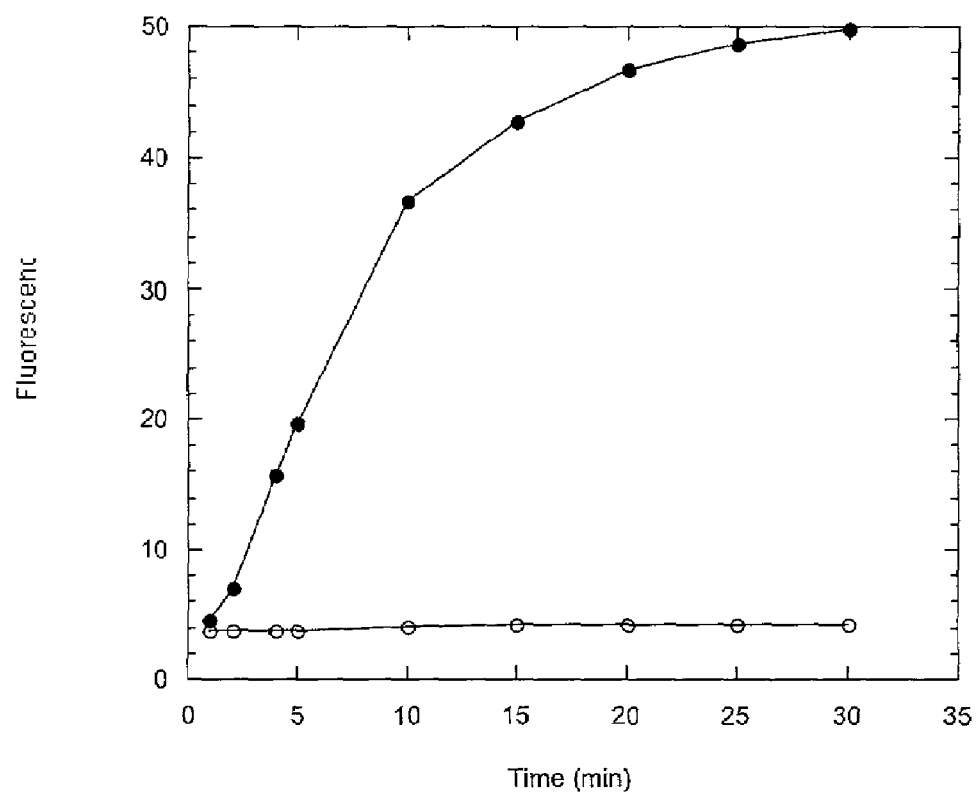
FIG. 5 shows ChePep-6 regulation of MMP-9 via the FRET assay. ChePep-6 is made by combining AFTA with a peptide having SEQ ID No. 8. ChePep-6 was incubated with MMP-9 for 10 minutes to effect binding. This mixture was added to the FRET substrate peptide in reaction buffer. Fluorescence measurements (Excitation 365 nm, Emission450 nm) were made at the indicated times. The curves represent ChepPep-6: MMP-9 molar stoichiometries of 0:1 (closed circles), 0.1:1 (open circles).
Figure 6:
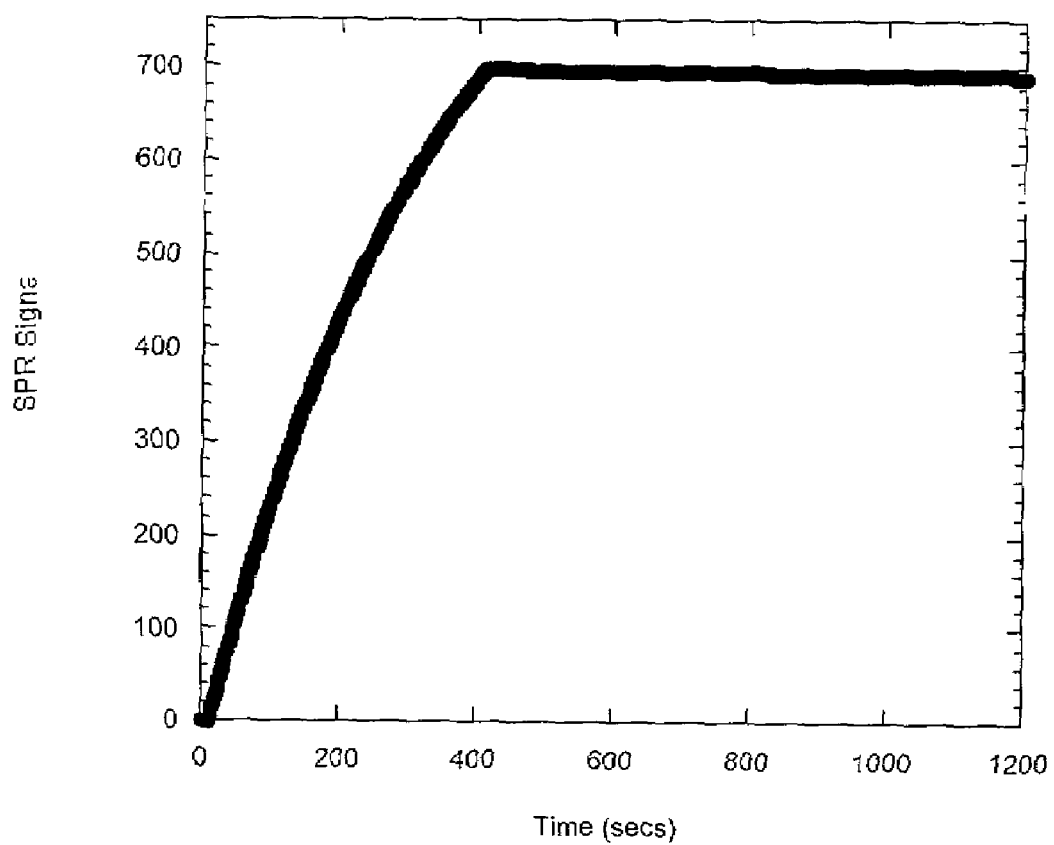
FIG. 6 depicts SPR analysis of ChePep-6 binding to immobilized MMP-9 that is on the surface of a BiaCoreCM-5 chip. The sensogram shows the relative SPR signal as a function of time for a 400 second association phase and an 800 second dissociation phase. Flow rate was maintained at a rate of 20 µL per minute.

This chelating peptide possesses the ability to prevent the hydrolysis of the FRET substrate peptide in the standard assay. As seen in FIG. 5, ChePep-6 is an effective MMP-9 regulator at low molar stoichiometries. In addition, ChePep-6 binds quickly and with high affinity; and once bound, ChePep-6 does not dissociate as seen in FIG. 6. In fact, the combination of a group I peptide and an AFTA moiety resulted in the most potent regulator of all the ChePeps.

In another aspect, the present invention comprises the treatment of chronic and acute wounds. By applying the composition to the chronic wound, MMP activity can be regulated. Specifically, the composition comprises a peptide with binding specificity to bring the zinc chelator into molecular proximity of the MMP bound zinc in such a way as to allow ligation. In addition to this affinity, the exact sequence of the peptide will allow targeting of specific MMPs. This chemistry regulates the level of MMP activity to a point that promotes healing.

A highlight of this peptide based therapy is the plasticity in which this material can be applied to a chronic wound. Where the infection is localized to the skin, a preferred formulation is an ointment, lotion or other topical formulation. The composition for topical application useful in the present invention can be made into a variety of product types. These include, but are not limited to, creams, gels, sticks, sprays, pastes, mousses, or any aqueous medium. These product types can comprise several types of carrier systems including, but not limited to, solutions, dispersions, emulsions, gels, solids, and liposomes. Additionally, the peptides can be introduced into the wound bed in a continuous manner via delivery by the wound bandage material itself. Preferred dose ranges for treatment of chronic wounds are between approximately 0.01 and 1.0 mg/mL Finally, another embodiment of the present invention is to control specific MMP activity. Certain diseases are caused by uncontrollable MMP activity. In fact, some diseases are caused by only a certain of the nine MMP molecules. By designing peptides that correspond with a specific MMP's active site, and then combining a zinc chelator to the peptide, only targeted MMP activity is regulated with a high degree of affinity and specificity.

The present invention is non-toxic in a skin equivalent model. The generally toxic effects of a non-specific zinc chelator are mitigated by the fact that the peptide portion of the ChePep construct directly targets the construct to the MMP active site in such a way as to minimize chelation at secondary (non MMP) targets.

The present invention is further illustrated and supported by the following examples. However, these examples should in no way be considered to further limit the scope of the invention. To the contrary, one having ordinary skill in the art would readily understand that there are other embodiments, modifications, and equivalents of the present invention without departing from the spirit of the present invention and/or the scope of the appended claims.

Basic Procedures

All peptides were synthesized by Sigma-Genosys, Inc. using conventional techniques. The released peptides were purified to >95% homogeneity via RP-HPLC by the company. The pooled eluted peak material was desalted and lyophilized. Mass Spec analysis confirmed the peptide molecular weight and purity. Unless otherwise noted, all chemicals were purchased from Sigma Chemical Corp. or from Fluka Chemical Co. Active MMP-9 enzyme was purchased from Calbiochem.

Molecular modeling utilized two visualization programs, Swiss PDB Viewer (Guex and Peitsch, 1997) and Rasmol (Sayle and Milner-White, 1995). Model work was performed on a Compaq PC running Windows 95, as well as a Silicon Graphics, Inc. Octane UNIX workstation. Additionally, the Cerius2 molecular package from Molecular Simulations, Inc. was utilized on the Octane. Three dimensional structure files were downloaded from the Protein Databank as follows (filename, reference): MMP-1 (1FBL, Li et al., 1995), MMP-2 (1GEN, Libson et al., 1995), MMP-8 (1JAO, 1JAN, Grams, et al., 1995; Reinemer et al., 1994), MMP-9 (1MMQ, Browner et al., 1995), TIMP-2/MT-1 MMP complex (1BUV, Femandez-Catalan et al., 1998), TIMP-2

(1BR9, Tuuttila et al., 1998), and TIMP-1/MMP complex (1UEA, Gomis-Ruth et al., 1997; Huang et al., 1996; Becker et al., 1995). These files were used to analyze the three-dimensional structure of the proteins, and the chemical nature and identification of conserved and variant amino acids in the MMP-TIMP contact interface. This information was utilized to design a minimalist peptide that could be coupled to a zinc chelator that would bind many MMP enzymes in the region of the catalytic zinc.

EXAMPLE 1

IDA Chelating Peptides

Peptide was resuspended in water to a final concentration of 100 mM. The amino form of IDA was dissolved in a small amount of DMSO followed by the slow addition of water until the compound was at a concentration of 150 mM. To the IDA solution was added N-hydroxysuccinimide (NHS), to a final concentration of 175 mM and N-ethyl-N'-(dimethylaminopropyl)-carbodiimide (EDC) to a final concentration of 400 mM. The solution was incubated at 37° C. with gentle stirring for 30 minutes. The previously prepared peptide solution was added to this reaction slowly over a period of 5 minutes. Stirring continued for an additional 30 minutes. The reaction was quenched by the addition of ethanolamine-HCl to a final concentration of 1.0 M. The final mixture was taken to dryness in a rotovac over a period of 10 hours. The solid material was then resuspended in 500 µL of water and the chelating peptide was purified away from unreacted species via RP-HPLC. A 250 mm×100 mm, 5 ml Hypersil ODS-2 RP column was chromatographed with a mobile phase of: A: 0.1% TFA/water, B: 0.1% TFA/acetonitrile. After sample injection, a gradient of 100% A (0 to 2 min) and 0–60% B (2 to 25 min) was applied. The chelating peptide was detected at 214 nm and was 96% pure by peak integration. The eluting peaks were pooled, mixed with 3 volumes of water, and lyophilized. The resulting powder was resuspended in water and dialyzed through a 500 MWCO cellulose acetate dialysis tube versus 50% phosphate buffered saline (PBS)/water. Chelating peptide was aliquoted and stored frozen at −20° C.

EXAMPLE 2

AFTA Chelating Peptides

AFTA (50 mg) was dissolved in a small amount of DMSO followed by the slow addition of water until the compound was at a concentration of 200 mM. To this solution was added zinc sulfate to a final concentration of 300 mM. This solution was stirred slowly at room temperature for 15 minutes. The sample was then treated with EDC/NHS as described in Example 1. The resulting AFTA-succinamide ester was coupled with a peptide having SEQ ID No. 7 or 8, and the resulting peptide was purified as discussed in Example 1. After lyophilization, the AFTA-peptide was resuspended in water, and it was extensively dialyzed versus water in a 500 MWCO cellulose acetate dialysis tube. The absence of zinc ion was confirmed by atomic absorption spectroscopy.

EXAMPLE 3

PSDE Chelating Peptides

PSDE was prepared according to the method of Hayward et al (1995). This material was coupled directly to a stoichiometric amount of a cysteine containing peptide having SEQ ID No. 4 or 6 by the following disulfide exchange reaction. PSDE in an amount of 100 mM in water and peptide in an amount of 100 mM in 25 mM Tris-HCl (pH 7.2) were mixed and allowed to react for 45 minutes at 30° C. The product was purified from the reactants by dialysis versus 10 mM Tris-HCl (pH 7.2) in a 500 MWCO cellulose acetate dialysis tube. The product was further purified by RP-HPLC as described in Example 1.

EXAMPLE 4

Regulation of MMPs

Two enzymatic assays were performed. The first assay measured the enzymatic hydrolysis of fluoresceinated collagen by MMP-9 as a function of time. Fluoresceinated collagen (Molecular Probes, Inc.), at a concentration of 5 µM was added to reaction buffer (50 mM Tris-HCl (pH 7.6), 150 mM NaCl, 5 mM $CaCl_2$, 0.1 mM $NaN_3$) and was placed into a Spectrosil quartz fluorometer cuvette. MMP at a concentration of 0.1 µM was mixed with varying amounts of chelating peptide having SEQ ID No. 4 or 6 and incubated at 25° C. for 10 minutes to effect binding. The protein mixture was added to the collagen substrate and mixed quickly. Fluorescence emission intensity at 520 nm was measured as a function of time (excitation wavelength 495 nm) in a Shimadzu RF5301 fluorometer. The fluorescein release assay was used to determine the inhibitory constant ($K_i$) of the chelating peptide inhibitor ([I]) according to Segel (1993) via the use of Dixon plots (1/v vs. [I]), such that:

$$\text{slope} = K_m/(V_{max} K_i [S]) \qquad (1)$$

where $K_m$ is the Michaelis constant, $V_{max}$ is the reaction maximum velocity, and [S] is the substrate concentration.

The second assay utilized the technique of fluorescence resonance energy transfer (FRET). The substrate peptide (Calbiochem #444221) comprised seven amino acids, coupled to a carboxyl terminal dinitrophenyl acceptor, and an amino terminal 2-aminobenzo-anthraniloyl (Abz) moiety donor. Cleavage of this substrate by MMP-9 results in the liberation of a fluorescent product (365 nm excitation, 450 nm emission). Peptide at a concentration of 5 µM was added to reaction buffer (50 mM Tris-HCl (pH 7.6), 150 mM NaCl, 5 mM $CaCl_2$, 0.1 mM $NaN_3$) and placed into a black 96-well microtiter plate well that had been previously blocked with 1% BSA. MMP at a concentration of 0.1 µM was mixed with varying amounts of chelating peptide (0, 0.01, 0.02, 0.04, and 0.1 µM) and incubated at 25° C. for 10 minutes to effect binding. The protein mixture was added to the peptide substrate and mixed quickly. Fluorescence intensity as a function of time was measured with a Dynex MFX fluorescence microtiter plate reader. Fluorescence intensity was related back to moles of peptide cleaved by producing a standard curve with an Abz containing non-FRET peptide. Inhibitory constants were derived from the curves and are listed below in Table 2.

TABLE 2

Inhibitor Constants

| Peptide | Sequence | Chelator | $K_i$ (µM) |
| --- | --- | --- | --- |
| ChePep-1 | CSAVPVH (SEQ ID No. 4) | PSDE | 98 |
| ChePep-2 | DSAVPVH (SEQ ID No. 5) | IDA | 67 |

TABLE 2-continued

Inhibitor Constants

| Peptide | Sequence | Chelator | $K_i(\mu M)$ |
|---|---|---|---|
| ChePep-3 | IYTACMSAV (SEQ ID No. 6) | PSDE | 350 |
| ChePep-4 | IYTACMSAV (SEQ ID No. 6) | IDA | 163 |
| ChePep-5 | VHTHLCD (SEQ ID No. 7) | AFTA | 221 |
| ChePep-6 | CTCVP (SEQ ID No. 8) | AFTA | 125 |

EXAMPLE 5

Surface Plasmon Resonance

The BiaCore-X surface plasmon resonance (SPR) device was utilized to measure the interaction between the chelating peptide (CP) and MMP-9. For these experiments a carboxymethyl dextran sensor chip (BiaCore, AB; CM-5, Lofas et al., 1993) was activated with 50 mM N-hydroxysuccinimide, 0.2 M N-ethyl-N'-(dimethylaminopropyl)-carbodiimide at a flow rate of 10 μL per minute for ten minutes. MMP-9 at a concentration of 75 ng/μL was coupled to the activated surface at a flow rate of 10 μL per minute for ten minutes. The final surface was inactivated by flowing 1 M ethanolamine HCl at a rate of 10 μL per minute for five minutes over the sensor surface. CP was flowed over the sensor surface at a rate of 20 μL per minute, and at concentrations of 10, 25, and 50 nM. Binding isotherms were evaluated by simultaneously fitting the forward ($k_a$) and reverse ($k_d$) rate constants to the following formula:

$$d[CP\sim MMP\text{-}9]/dt = (k_a[CP][MMP\text{-}9]) - (k_d[CP\sim MMP\text{-}9]) \quad (2)$$

(Karlsson and Falt, 1997) where [CP], [MMP-9], and [CP~MMP-9] are the concentrations of free chelating peptide, free MMP-9, and the complex respectively. The equilibrium affinity constant ($K_A$) is defined as:

$$K_A = k_a/k_d \quad (3)$$

Equation 3 is expressed in terms of the SPR signal (Mortonet al., 1995) as:

$$dR/dt = k_a C R_{max} - (k_a C + k_d) R \quad (4)$$

where R is the SPR signal (in response units, RU) at time t, $R_{max}$ is the maximum MMP-9 binding capacity in RU, and C is the chelating peptide concentration. Kinetic analysis (O'Shannessy et al., 1993) was performed using Origin from Microcal, Inc.

EXAMPLE 6

Viability Assays

The relative toxicity of the chelating and substrate peptides was assayed using the skin model Epiderm that is commercially available from MatTek Corp. The individual skin sample containers were preincubated in culture medium at 37° C. under 5% $CO_2$ for two hours prior to the addition of the peptide constructs. The sample containers were transferred to 6 well plates that contained fresh media. All peptides were dissolved in PBS at a final concentration of 10 mM, and 100 μL of each peptide solution was pipetted onto the surface of the Epiderm sample container. Incubation was continued for 12 hours at 37° C. under 5% $CO_2$. After the incubation period, the sample containers were washed three times with PBS and the sample containers were transferred to a 24 well plate that contained 300 μL of MTT assay media per well (MTT concentration was 1 mg/mL). The colorimetric assay was allowed to develop for three hours (incubation at 37° C. under 5% $CO_2$). Sample containers were then transferred to a 24 well culture plate that contained 2 mL of isopropanol per well. Extraction of the colored precipitate occurred over a period of four hours at room temperature. Absorbance readings were taken at 570 nm and 650 nm for each sample. The percent viability of each sample relative to a PBS control was calculated as:

$$100 \times (OD_{570}^{sam} - OD_{650}^{sam})/(OD_{570}^{con} - OD_{650}^{con}) \quad (5)$$

Routinely, each peptide sample was assayed in duplicate or triplicate.

EXAMPLE 7

Figure 7:
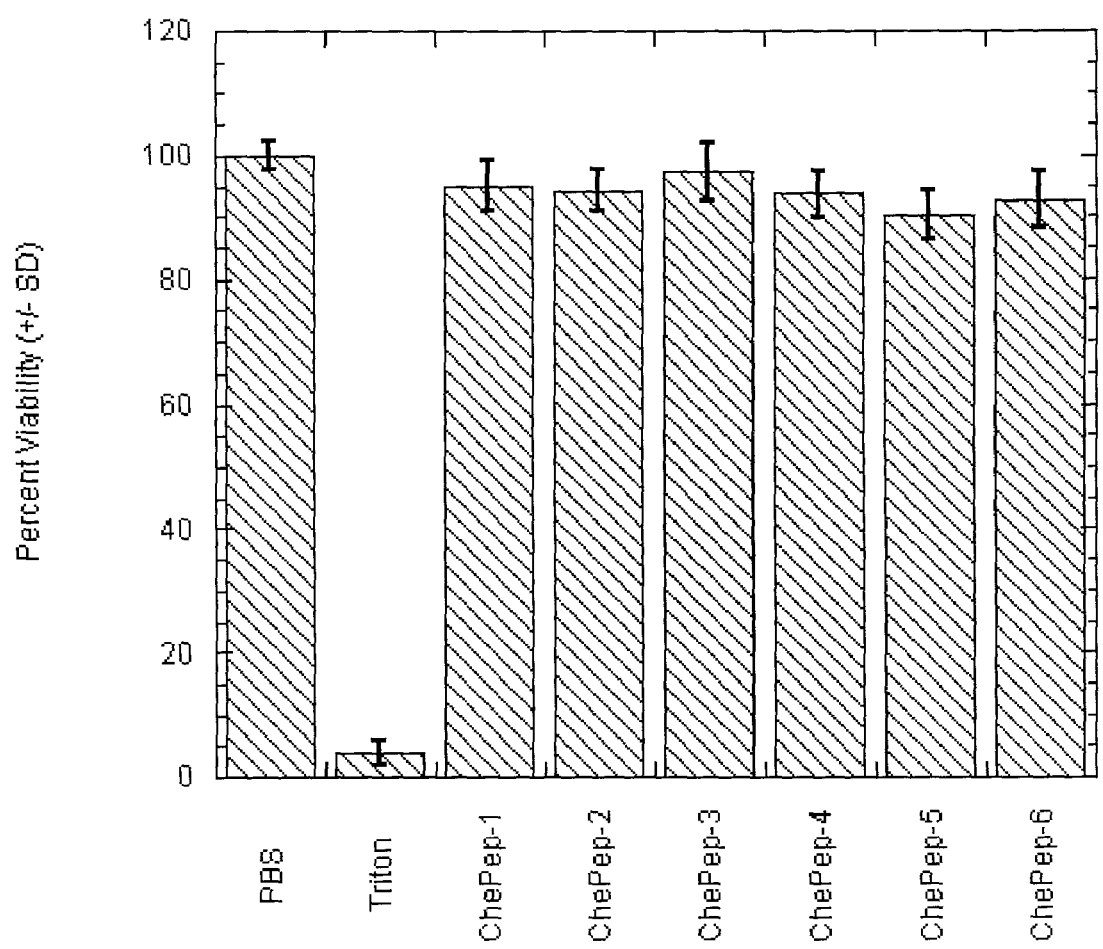
FIG. 7 represents compound viability assays. The graph plots the percent viability of the peptides utilized in this study relative to a PBS control. Error bars are +/−SD. Samples (left to right) are as follows: PBS positive control, 1%Triton X-100 negative control, ChePep-1, ChePep-2, ChePep-3, ChePep-4, ChePep-5, and ChePep-6.

A skin equivalent toxicity model (Epiderm) was employed to measure the overall cellular viability in the presence of the six peptide constructs. A single dose of 10 mM peptide (in PBS) was applied to the Epiderm samples for a period of 12 hours. The resulting viability is plotted in FIG. 7. A PBS control is set to a value of 100 percent viability. The surfactant Triton X-100 served as a negative control, that is the application of a 1% triton solution should result in over 90% cell death. As can be seen in FIG. 7, all six peptides exhibit about 94.2+/−3.8 percent. Of the three zinc chelators, AFTA seems to be slightly more toxic (90.5% viability) than IDA (94.8% viability) or PSDE (96.5% viability), although the viability differences are not significant.

We claim:

1. A metalloproteinase regulator comprising a 2-amino-4-fluorophenol N,N,O triacetic acid zinc chelator covalently attached to the N-terminus of a TIMP-derived peptide consisting essentially of SEQ ID NO:8.

2. A method of treating chronic or acute wounds comprising administering a metalloproteinase regulator comprising a 2-amino-4-fluorophenol N,N,O triacetic acid zinc chelator covalently attached to the N-terminus of a TIMP-derived peptide consisting essentially of SEQ ID NO:8.

3. A composition comprising a pharmaceutically acceptable carrier and a metalloproteinase regulator, wherein the metalloproteinase regulator comprises a 2-amino-4-fluorophenol N,N,O triacetic acid zinc chelator covalently attached to the N-terminus of a TIMP-derived peptide consisting essentially of SEQ ID NO:8.

4. The composition of claim 3, wherein the composition is in topical form.

5. The composition of claim 3, wherein the composition is in the form of a lotion, ointment, cream, gel, stick, spray, paste, mousse, solution, dispersion, emulsion, solid or liposome.

* * * * *